(12) United States Patent
Crainich et al.

(10) Patent No.: US 9,724,162 B2
(45) Date of Patent: Aug. 8, 2017

(54) APPARATUS AND METHOD FOR CONTROLLING AN END-EFFECTOR ASSEMBLY

(71) Applicant: TITAN MEDICAL INC., Toronto (CA)

(72) Inventors: Lawrence Crainich, Charlestown, NH (US); Alexander Shvartsberg, Oakville (CA)

(73) Assignee: TITAN MEDICAL INC., Toronto (CA)

( * ) Notice: Subject to any disclaimer, the term of this patent is extended or adjusted under 35 U.S.C. 154(b) by 381 days.

(21) Appl. No.: 14/261,614

(22) Filed: Apr. 25, 2014

(65) Prior Publication Data

US 2014/0276956 A1 Sep. 18, 2014

Related U.S. Application Data

(63) Continuation of application No. PCT/CA2011/001226, filed on Nov. 4, 2011.

(51) Int. Cl.
*A61B 17/29* (2006.01)
*A61B 19/00* (2006.01)
*A61B 34/00* (2016.01)
*A61B 17/22* (2006.01)
*B25J 9/10* (2006.01)
(Continued)

(52) U.S. Cl.
CPC .......... *A61B 19/2203* (2013.01); *A61B 34/30* (2016.02); *A61B 34/71* (2016.02); *A61B 17/22031* (2013.01); *A61B 2017/00991* (2013.01); *A61B 2017/22038* (2013.01); *A61B 2034/301* (2016.02); *A61B 2034/305* (2016.02);
(Continued)

(58) Field of Classification Search
CPC .... A61B 17/22031; A61B 2017/22038; A61B 2034/305; A61B 34/71
USPC ............... 901/31; 74/89.22, 490.04; 606/205
See application file for complete search history.

(56) References Cited

U.S. PATENT DOCUMENTS 5,382,885 A 1/1995 Salcudean et al.
5,390,678 A 2/1995 Gesswein
(Continued)

FOREIGN PATENT DOCUMENTS

CA 1239167 A 7/1988
CA 2222150 C 9/2008
(Continued)

OTHER PUBLICATIONS

Extended European Search Report dated Mar. 19, 2015 for European Patent Application No. 11874984.
(Continued)

*Primary Examiner* — William C Joyce
*Assistant Examiner* — Randell J Krug
(74) *Attorney, Agent, or Firm* — Perry + Currier Inc.

(57) ABSTRACT

An apparatus for controlling an end-effector assembly having a first working member and a second working member is provided. The apparatus includes a first set of at least one cable, a second set of at least one cable, a first pulley configured to guide the first set of at least one cable, a second pulley configured to guide the first set of at least one cable when the second pulley is in a first position, a third pulley configured to guide the second set of at least one cable, and a rotatable element rotatable about a first axis.

24 Claims, 19 Drawing Sheets

(51) Int. Cl.
  *B25J 15/00* (2006.01)
  *B25J 9/00* (2006.01)
  *A61B 17/00* (2006.01)
  *A61B 34/30* (2016.01)

(52) U.S. Cl.
  CPC .............. *B25J 9/0078* (2013.01); *B25J 9/104* (2013.01); *B25J 15/0028* (2013.01)

(56) References Cited

U.S. PATENT DOCUMENTS

| | | | |
|---|---|---|---|
| 5,749,362 A | 5/1998 | Funda et al. | |
| 5,797,900 A * | 8/1998 | Madhani | B25J 3/04 606/1 |
| 5,891,020 A | 4/1999 | Luber et al. | |
| 6,132,368 A | 10/2000 | Cooper | |
| 6,245,028 B1 | 6/2001 | Furst et al. | |
| 6,264,665 B1 | 7/2001 | Yu et al. | |
| 6,471,172 B1 | 10/2002 | Lemke | |
| 6,620,173 B2 | 9/2003 | Gerbi et al. | |
| 6,676,684 B1 * | 1/2004 | Morley | A61B 34/71 606/205 |
| 6,685,698 B2 * | 2/2004 | Morley | A61B 17/062 606/1 |
| 6,699,177 B1 | 3/2004 | Wang et al. | |
| 7,048,745 B2 * | 5/2006 | Tierney | G06Q 30/02 606/1 |
| 7,118,582 B1 | 10/2006 | Wang et al. | |
| 7,331,967 B2 | 2/2008 | Lee et al. | |
| 7,419,080 B2 | 9/2008 | Smith et al. | |
| 7,608,083 B2 | 10/2009 | Lee et al. | |
| 7,666,191 B2 | 2/2010 | Orban, III et al. | |
| 7,695,481 B2 | 4/2010 | Wang et al. | |
| 7,867,241 B2 | 1/2011 | Brock et al. | |
| 7,918,826 B2 | 4/2011 | Armstrong et al. | |
| 7,963,913 B2 | 6/2011 | Devengenzo et al. | |
| 8,540,748 B2 * | 9/2013 | Murphy | A61B 34/71 606/205 |
| 2002/0045888 A1 * | 4/2002 | Ramans | A61B 19/2203 606/1 |
| 2002/0111621 A1 * | 8/2002 | Wallace | A61B 34/71 606/41 |
| 2003/0208186 A1 * | 11/2003 | Moreyra | A61B 34/30 606/1 |
| 2004/0199147 A1 * | 10/2004 | Nishizawa | A61B 17/062 606/1 |
| 2006/0161136 A1 | 7/2006 | Anderson et al. | |
| 2006/0235436 A1 | 10/2006 | Anderson et al. | |
| 2007/0088340 A1 | 4/2007 | Brock et al. | |
| 2007/0208375 A1 * | 9/2007 | Nishizawa | A61B 17/29 606/205 |
| 2008/0077159 A1 * | 3/2008 | Madhani | A61B 17/00234 606/130 |
| 2008/0147089 A1 | 6/2008 | Loh et al. | |
| 2008/0213077 A1 | 9/2008 | Tanaka et al. | |
| 2009/0088774 A1 * | 4/2009 | Swarup | A61B 34/37 606/130 |
| 2009/0248039 A1 | 10/2009 | Cooper et al. | |
| 2010/0042142 A1 | 2/2010 | Cunningham | |
| 2010/0198253 A1 * | 8/2010 | Jinno | A61B 17/29 606/205 |
| 2010/0268249 A1 | 10/2010 | Stuart | |
| 2011/0106145 A1 * | 5/2011 | Jeong | A61B 17/29 606/205 |
| 2011/0174860 A1 | 7/2011 | Shelton, IV et al. | |
| 2011/0277775 A1 | 11/2011 | Holop et al. | |
| 2012/0330287 A1 * | 12/2012 | Yim | A61B 34/70 606/1 |
| 2014/0350570 A1 * | 11/2014 | Lee | A61B 17/2909 606/130 |

FOREIGN PATENT DOCUMENTS

| | | |
|---|---|---|
| EP | 1886633 A2 | 2/2008 |
| EP | 2366342 A1 | 9/2011 |
| GB | 2239605 A | 7/1991 |
| WO | 98/25666 A1 | 6/1998 |
| WO | 00/30548 A1 | 6/2000 |
| WO | WO-02051329 A1 | 7/2002 |
| WO | 2004070400 A1 | 8/2004 |
| WO | 2009157719 A2 | 12/2009 |
| WO | 2010090292 A2 | 8/2010 |

OTHER PUBLICATIONS

Related PCT Application No. PCT/CA2011/001225 International Search Report dated Jul. 26, 2012.
Related PCT Application No. PCT/CA2011/001225 Written Opinion of the International Searching Authority dated Jul. 26, 2012.
Corresponding PCT Application No. PCTCA2011/001226 International Search Report dated Jul. 17, 2012.
Corresponding PCT Application No. PCTCA2011/001226 Written Opinion of the International Searching Authority dated Jul. 17, 2012.
Related PCT Application No. PCT/CA2011/001302 International Search Report dated Aug. 31, 2012.
Related PCT Application No. PCT/CA2011/001302 Written Opinion of the International Searching Authority dated Aug. 31, 2012.
Related PCT Application No. PCT/CA2011/001303 International Search Report dated Aug. 17, 2012.
Related PCT Application No. PCT/CA2011/001303 Written Opinion of the International Searching Authority dated Aug. 17, 2012.
Related PCT Application No. PCT/CA2011/001386 International Search Report dated Aug. 13, 2012.
Related PCT Application No. PCT/CA2011/001386 Written Opinion of the International Searching Authority dated Aug. 13, 2012.

* cited by examiner

APPARATUS AND METHOD FOR CONTROLLING AN END-EFFECTOR ASSEMBLY

FIELD

The present specification here relates in general to a field of robotic instruments, and more particularly, to a robotic system for use in surgery.

BACKGROUND

With the gradual transition of medical surgery from the conventional process of making a long incision in the patient's body for performing a surgery to the next generation of surgery, i.e. minimal invasive surgery (MIS), continuous research is going on to develop and integrate robotic instruments in a system which can be used for MIS purposes. Such integration can help a surgeon perform a surgery in an error-free manner, and at the same time work in a realistic environment that gives the surgeon a feel of conventional surgery.

SUMMARY

In accordance with an aspect of the invention, there is provided an apparatus for controlling an end-effector assembly having a first working member and a second working member. The apparatus includes a first set of at least one cable. The first set of at least one cable is configured to control the first working member. The apparatus also includes a second set of at least one cable. The second set of at least one cable is configured to control the second working member. The apparatus further includes a first pulley configured to guide the first set of at least one cable. In addition, the apparatus includes a second pulley configured to guide the first set of at least one cable when the second pulley is in a first position. The second pulley is configured to guide the second set of at least one cable when the second pulley is in a second position. Furthermore, the apparatus includes a third pulley configured to guide the second set of at least one cable. The apparatus also includes a rotatable element rotatable about a first axis. The rotatable element supports the first pulley, the second pulley, the third pulley, and the first and second working members, and the rotatable element configured to move the second pulley between the first position and the second position.

The first pulley can be configured to rotate about a first pulley axis, The second pulley can be configured to rotate about a second pulley axis. The third pulley can be configured to rotate about a third pulley axis.

The first pulley axis, the second pulley axis, and the third pulley axis can be spaced apart.

The first pulley axis, the second pulley axis, and the third pulley axis can be equidistant from the first axis.

The first pulley axis, the second pulley axis, and the third pulley axis can be rotatable about the first axis.

The first pulley, the second pulley, and the third pulley can be configured to rotate in a first pulley plane.

The first pulley plane can be perpendicular the first axis.

The apparatus can further include a third set of at least one cable. The third set of at least one cable can be configured to rotate the rotatable element about the first axis to adjust a rotation about the first axis.

The rotatable element can include a ball portion, the ball portion configured to rotate in a socket.

The rotatable element can include a cylindrical portion. An axis of the cylindrical portion can coincide with the first axis.

The rotatable element can include an insulating material.

At least one set of at least one cable can be electrically conductive. The at least one set of at least one cable can be configured to deliver an electrical current to at least one working member.

The apparatus can further include a first pair of pulleys. The first pair of pulleys can include the first pulley and a fourth pulley.

The first pulley and the fourth pulley can be configured to rotate about the first pulley axis.

The apparatus can further include a second pair of pulleys. The second pair of pulleys can include the second pulley and a fifth pulley.

The second pulley and the fifth pulley can be configured to rotate about the first pulley axis.

The apparatus can further include a third pair of pulleys. The third pair of pulleys can include the third pulley and a sixth pulley.

The third pulley and the sixth pulley can be configured to rotate about the third pulley axis.

The fourth pulley, fifth pulley and sixth pulley can be configured to rotate in a second pulley plane.

The second pulley plane can be perpendicular the first axis.

In accordance with an aspect of the invention, there is provided a method for guiding cables. The method involves guiding a first set of at least one cable between a first pair of pulleys and a second pair of pulleys such that the first set of at least one cable is in contact with at least one of the first pair of pulleys and the second pair of pulleys. The first set of at least one cable is configured to control a first working member. The method also involves guiding a second set of at least one cable between the second pair of pulleys and a third pair of pulleys such that the second set of at least one cable is in contact with at least one of the second pair of pulleys and the third pair of pulleys. The second set of at least one cable is configured to control a first working member.

BRIEF DESCRIPTION OF THE DRAWINGS

Reference will now be made, by way of example only, to the accompanying drawings in which.

DETAILED DESCRIPTION OF THE EMBODIMENTS

Figure 1:
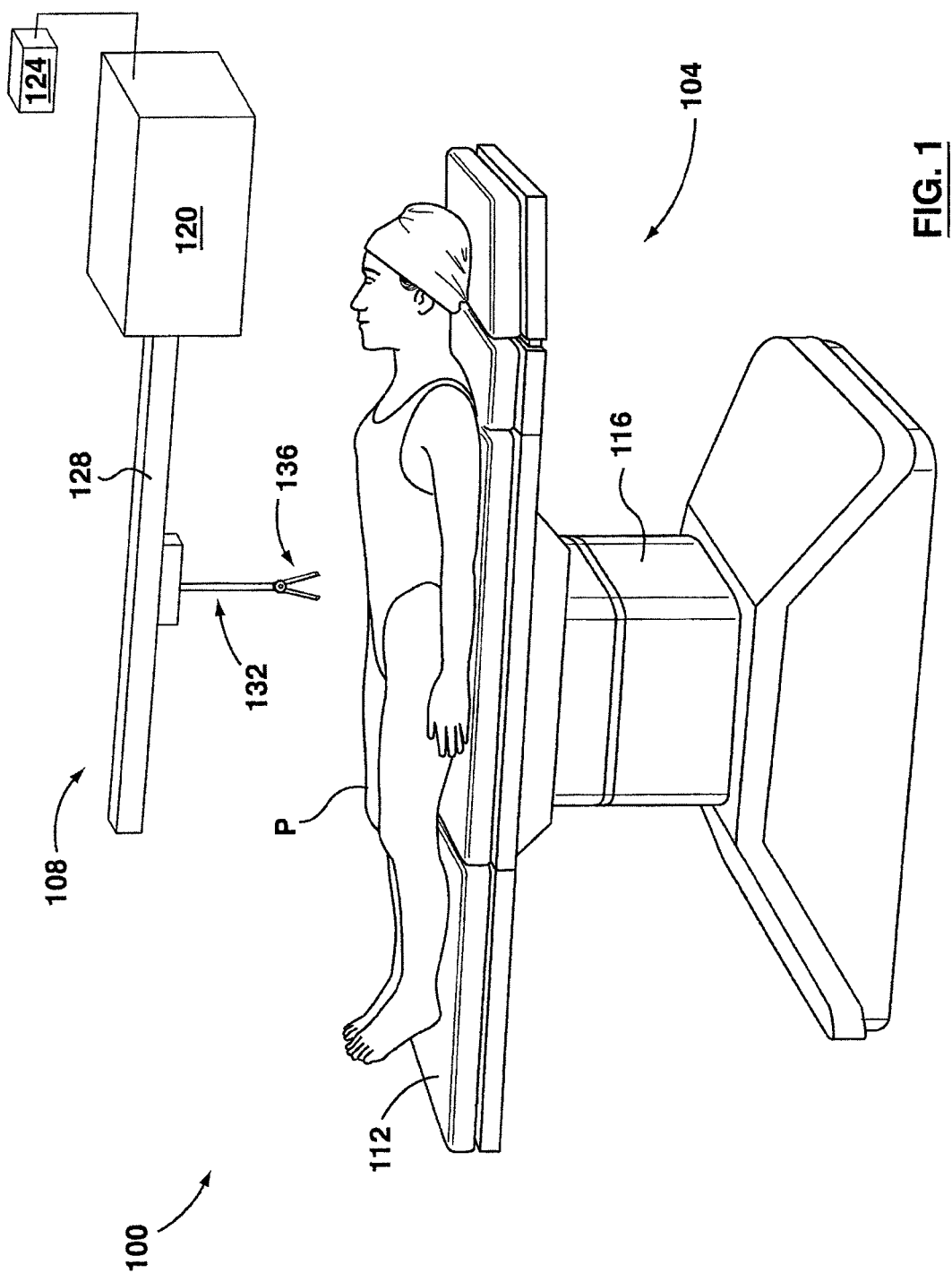
FIG. 1 is a perspective view of an operating theater according to an embodiment.

Referring to FIG. 1, a schematic representation of an operating theater for Minimal Invasive Surgery (MIS) is shown at 100. It is to be understood that the operating theater 100 is purely exemplary and it will be apparent to those skilled in the art that a variety of operating theaters are contemplated. The operating theater 100 includes a surgical table 104 and a surgical system 108. The surgical table 104 includes a surface 112 supported by a base 116. It is to be understood that the surgical table 104 is not particularly limited to any particular structural configuration. A patient P rests on the surface 112. The surgical system 108 includes a base unit 120, an input device 124, a robotic arm 128, and at least one robotic instrument 132 with an end-effector assembly 136.

In a present embodiment, the base unit 120 is generally configured to support and control the robotic arm 128 in response to input control signals from input device 124 under the control of a surgeon or other medical professional. In terms of providing physical support, the base unit 120 is mechanically structured to support the robotic arm 128, the robotic instrument 132, and their associated movement. For example, the base unit 120 can be bolted to a fixed structure such as a wall, floor, or ceiling. Alternatively, the base unit 120 can have a mass and a geometry such that when base unit 120 is free-standing, it will support the robotic arm 128. In some embodiments, the base unit 120 can include a moveable cart to provide easy movement of the base unit 120 around the operating theater 100. In terms of providing control, the base unit 120 can include mechanical controls (not shown), or electrical controls (not shown), or both. For example, mechanical controls can include gears, cables or other motion transfer mechanisms (not shown) connected to a motor. Other mechanical controls can also involve hydraulics. Alternatively, in embodiments where a motor is disposed in the robotic arm 128 or the robotic instrument 132, the base unit 120 can supply only electrical control signals to operate the motors in the robotic arm 128 or the robotic instrument.

Referring again to FIG. 1, the robotic arm 128 is generally configured to support the robotic instrument 132. In terms of providing physical support, the robotic arm 128 is mechanically structured to support the robotic instrument 132, and its associated movement. For example, the robotic arm 128 is constructed such that it is rigid enough to be suspended above the patient P. In addition, the robotic arm 128 can be configured so that robotic instrument 132 is positionable in relation to the base unit 120 and surface 112. For example, the robotic arm 128 can include a moveable joint (not shown) for providing a pivotal degree of freedom. In other example, the robotic arm 128 can include a rail system (not shown) for linear movement of the robotic instrument 132. It will now be understood that the movement of the robotic arm 128 is controlled by the base unit 120 through various controls described above.

In general terms, the robotic instrument 132 and its end-effector assembly 136 are generally configured for performing MIS responsive to inputs from the input device 124 mediated by the base unit 120 and the robotic arm 128. However, it is to be re-emphasized that the structure shown in FIG. 1 is a schematic, non-limiting representation only. For example, although only one robotic arm 128 is shown in FIG. 1, it is to be understood that the surgical system 108 can be modified to include a plurality of robotic arms 128, each robotic arm 128 having its own a separate robotic instrument 132 and separate end-effector assembly 136. Furthermore, it is also to be understood that where the surgical system 108 includes a plurality of robotic arms 128 with robotic instruments 132, each robotic arm 128 or robotic instrument 132 can have different structures. Indeed, a plurality of different configurations of robotic instrument 132 are contemplated herein.

In use, the robotic instrument 132 is configured to provide the end-effector assembly 136 with at least one degree of freedom. A degree of freedom refers to an ability of an end-effector assembly 136 to move according to a specific motion. For example, a degree of freedom can include a rotation of the end-effector assembly 136 or a component thereof about a single axis. Therefore, for each axis of rotation, the end-effector assembly 136 is said to have a unique degree of freedom. Another example of a degree of freedom can include a translational movement along a path. It will now be apparent that each additional degree of freedom increases the versatility of the end-effector assembly 136. By providing more degrees of freedom, it will be possible to position the end-effector assembly 136 in a wider variety of positions or locations to, for example, reach around obstacles.

Figure 2:
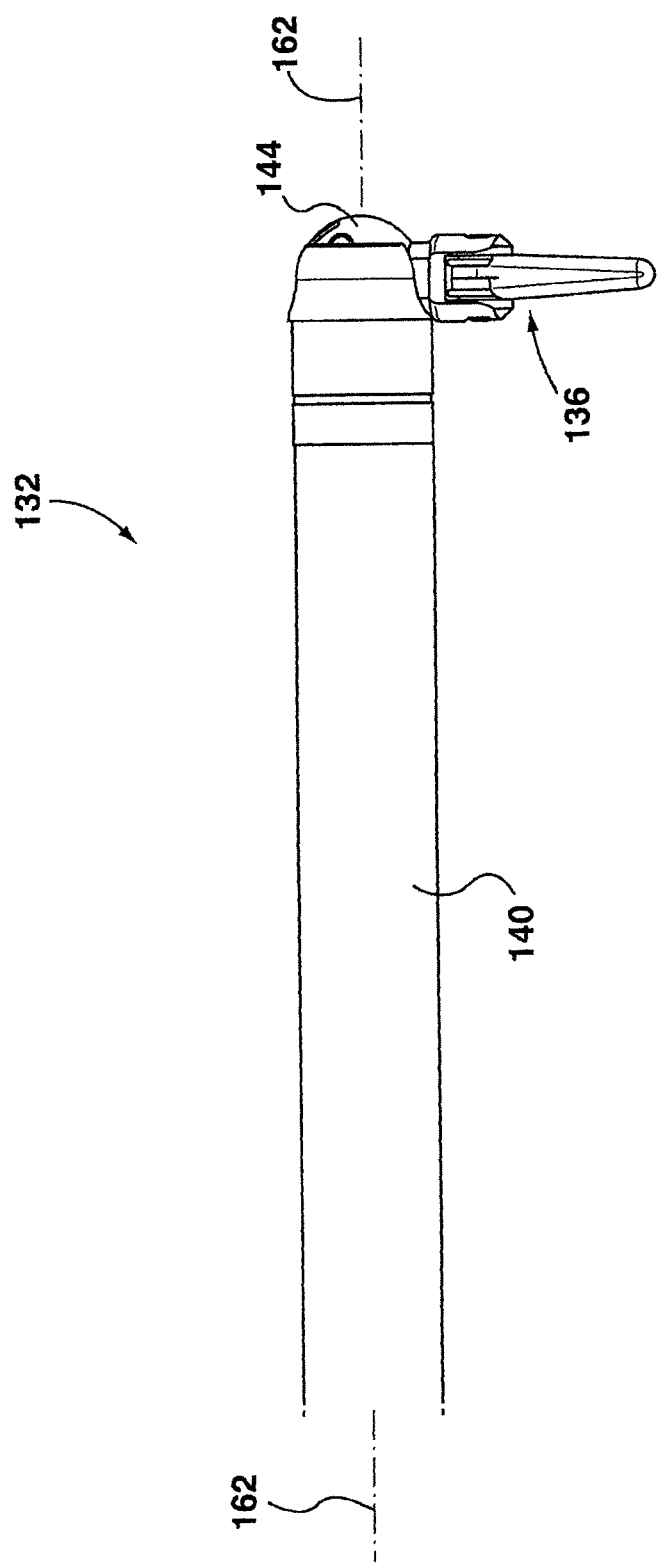
FIG. 2 is a perspective view of a robotic instrument in accordance with an embodiment.

Referring to FIGS. 2 to 12, an embodiment of the robotic instrument 132 is shown in greater detail. It is to be understood that the robotic instrument 132 (as shown in FIG. 2) is purely exemplary and it will be apparent to those skilled in the art that a variety of robotic instruments are contemplated including other embodiments discussed in greater detail below. The robotic instrument 132 includes an end-effector assembly 136, an elongated element 140, and a rotatable element 144.

In the present embodiment, the end-effector assembly 136 is generally configured to interact with the patient P during MIS. The end-effector assembly 136 includes two working members 148 and 152. It is to be understood that the end-effector assembly 136, including the working members 148 and 152, is not particularly limited to any material and that several different types of materials are contemplated. The end-effector assembly 136 is typically constructed from materials which can withstand the harsh conditions of a sterilization process carried out prior to an actual surgery. Some examples of suitable materials include stainless steel, such as surgical stainless steel, titanium, plastics, composites and other materials commonly used in surgical instruments. The exact configuration of working members 148 and 152 is not particularly limited. In the present embodiment, the working members 148 and 152 are the jaws of forceps. In other embodiments, the working members can be other surgical instruments such as scissors, blades, graspers, clip appliers, staplers, retractors, clamps or bi-polar cauterizers or combinations thereof. Also, in other embodiments the end-effector assembly may include a single working member such as imaging equipment, such as a camera or light source, or surgical instruments such as scalpels, hooks, needles, catheters, spatulas or mono-polar cauterizers.

Referring to FIG. 2, the elongated element 140 extends between the end-effector assembly 136 and the robotic instrument base (not shown). The elongated element 140 is generally configured to support the end-effector assembly 136 and to guide first and second sets of cables 156 and 160 from the robotic instrument base to the end-effector assembly 136. In addition, the elongated element 140 can be configured to rotate about an axis 162. The first and second set of cables 156 and 160 can comprise a single cable or a plurality of cables. It is to be understood that the elongated element 140 and the first and second set of cables 156 and 160 are not particularly limited to any material and that several different types of surgical-grade materials are contemplated. Examples of surgical grade materials include surgical stainless steel, titanium, plastics, composites and other materials commonly used in surgery, which in general can withstand sterilization. However, as will be discussed later, it can be advantageous for the first and second set of cables 156 and 160 to be made from an electrically conductive material such as a metal wire as in the present embodiment.

Figure 9:
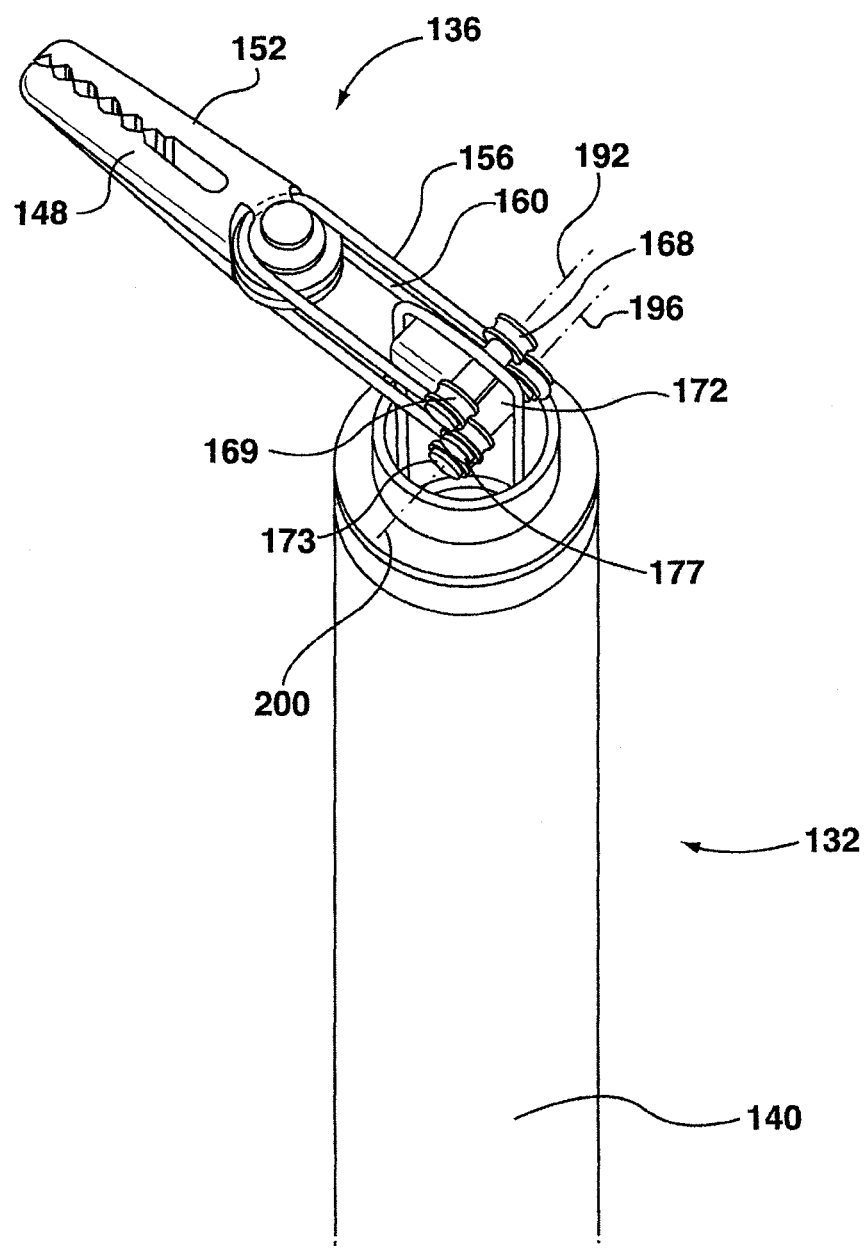
FIG. 9 is a perspective view of the internal parts of the robotic instrument of FIG. 2.

Referring to FIGS. 5-9, the rotatable element 144 of the present embodiment generally includes a spherical ball portion configure to rotate in a socket disposed at an end of the elongated element 140. The rotatable element 144 is configured to rotate only about a first axis 164 and to support first, second and third pulleys 168, 172 and 176 as well as the working members 148 and 152 of the end-effector assembly 136. The first, second and third pulleys 168, 172 and 176 are generally configured to rotate about first, second and third pulley axes 192, 196, and 200, respectively, and to guide the first and second set of cables 156 and 160 such that the cables can move with little friction when the end-effector assembly 136 is in various positions. Alternatively, stationary capstans may be used in place of the pulleys for slidably engaging the cables. In the present embodiment, the rotatable element 144 can be configured to further support fourth, fifth and sixth pulleys 169, 173 and 177. It is to be now appreciated that the fourth, fifth and sixth pulleys 169, 173 and 177 are for guiding a separate segment of the first and second sets of cables 156 and 160 such that applying tension to this segment applies a rotational torque on the working members 148 and 152 in the opposite direction from applying tension to the segment guided by first, second and third pulleys 168, 172 and 176. As shown in FIG. 9, the first pulley 168 and fourth pulley 169 can be configured to be a first connected pair of pulleys rotating about a first pulley axis 192. Similarly, the second pulley 172 and fifth pulley 173 can be configured to be a second connected pair of pulleys rotating about a second pulley axis 196. The third pulley 176 and sixth pulley 177 can be configured to be a third connected pair of pulleys rotating about a third pulley axis 200.

In the present embodiment shown in FIGS. 2-9, the first, second and third pulleys 168, 172 and 176 are tightly spaced together such that the overall size of the rotatable element 144 is reduced. Furthermore, the first, second and third pulleys 168, 172 and 176 can be configured such that the first, second and third pulleys 168, 172 and 176 rotate within the same plane, which will be referred to as the first pulley plane. Similarly, the fourth, fifth and sixth pulleys 169, 173 and 177 can be configured such that the fourth, fifth and sixth pulleys 169, 173 and 177 rotate within the same plane, which will be referred to as the second pulley plane. It is to be understood that the rotatable element 144, including the plurality of pulleys, is not particularly limited to any material and that several different types of surgical-grade materials are contemplated. Examples of surgical grade materials include surgical stainless steel, titanium, plastics, composites and other materials commonly used in surgery, which in general can withstand sterilization. However, as will be discussed later, it can be advantageous for the rotatable element 144 to be made from an insulating material such as plastic as in the present embodiment. Furthermore, in the present embodiment, the first, second and third pulleys 168, 172 and 176 are identical in size and positioned to be equidistant from the first axis 164. In other embodiments, the rotatable element 144 can be modified such that the first, second and third pulleys 168, 172 and 176 are positioned according to another configuration. For example, the first, second and third pulleys 168, 172 and 176 can be placed on a straight line. Furthermore, in other embodiments, the first, second and third pulleys 168, 172 and 176 can be modified to be different sizes.

In operation, the present embodiment of the robotic instrument 132 controls the movement of the working members 148 and 152 of the end-effector assembly 136. The first set of cables 156 is generally configured to control motion of the first working member 148 about a second axis 180. In the present embodiment the first set of cables includes a pair of cables. Each of the pair of cables is connected to the first working member 148 such that the two cables would provide torque in opposite directions when tension is applied to the cable. Therefore, applying tension to one cable will apply a torque to the working member 148 in a first direction about the second axis 180 and applying tension to the other cable will apply a torque to the working member 148 in a second direction about the second axis 180 that is opposite to the first direction. The second set of cables 160 is generally configured to control motion of the second working member 152 about the second axis 180. It is to be understood that the second set of cables 160 can be controlled independently from the first set of cables 156. In the present embodiment the second set of cables 160 includes a pair of cables. Each of the pair of cables is connected to the second working member 152 such that the two cables would provide torque in opposite directions when tension is applied to the cable. Therefore, applying tension to one cable will apply a torque to the working member 152 in a first direction about the second axis 180 and applying tension to the other cable will apply a torque to the working member 152 in a second direction about the second axis 180 that is opposite to the first direction. It will now be appreciated that one of the two cables from each set of cables 156 and 160 is guided by the first, second and third pulleys 168, 172, and 176 whereas the other cable is guided by the fourth, fifth and sixth pulleys 169, 173, and 177. In other embodiments, first and second set of cables 156 and 160 can include a single cable looped around the first and second working members 148 and 152, respectively, such that frictional engagement between the cable and the working member will provide torque to rotate the working members 148 and 152 about the second axis 180. Therefore, first and second set of cables 156 and 160 each provides a degree of freedom which involves rotating the first and second working members 148 and 152, respectively about a second axis 180.

In addition, the rotatable element 144 can be controlled with a third set of cables 184. The third set of cables controls the rotatable element 144 and rotates the rotatable element about the first axis 164 in substantially the same manner the first and second set of cables 156 and 160 controls the first and second working members 148 and 152, respectively. Therefore, the rotatable element 144 can be positioned at a variety of angles including a first position (shown in FIGS. 5 and 6), a second position (shown in FIG. 7), and an intermediate position (shown in FIG. 8). It is to be understood that when the rotatable element 144 is rotated about the first axis 164, the first, second and third pulleys 168, 172 and 176 are collectively rotated about the first axis 164. In the present embodiment, the first, second and third pulleys 168, 172 and 176 each guide the first and second set of cables 156 and 160 regardless of the position of the rotatable element 144. It will now be appreciated that due to the tension of the first and second set of cables 156 and 160, the force applied to the first, second and third pulleys 168, 172 and 176 will not be equal. For example, when the rotatable element 144, including the first, second and third pulleys 168, 172 and 176, is in the first position, the second pulley 172 applies more force than the first pulley 168 to the first set of cables 156. Similarly, the third pulley 176 applies more force than the second pulley 172 to the second set of cables 160. When the rotatable element 144, including the first, second and third pulleys 168, 172 and 176, is in the second position, the second pulley 172 applies more force than the third pulley 176 to the second set of cables 160. Similarly, the first pulley 168 applies more force than the second pulley 172 to the first set of cables 156. It will now be appreciated that the second pulley 172 will bear the higher forces in both the first and second position whereas the first and third pulleys 168 and 176 only bear the higher forces in one of the two positions discussed.

It will also be appreciated that by configuring the first, second and third pulleys 168, 172 and 176 to rotate in the pulley plane, the transition between various positions of the rotatable element 144 is facilitated. In the present embodiment, the first and second pulley planes are configured to be perpendicular to the first axis 164. Therefore, it is to be understood that in this configuration, the pulley plane does not move relative to the robotic instrument 132 as the rotatable element 144 is rotated about the first axis 164.

Figure 3:
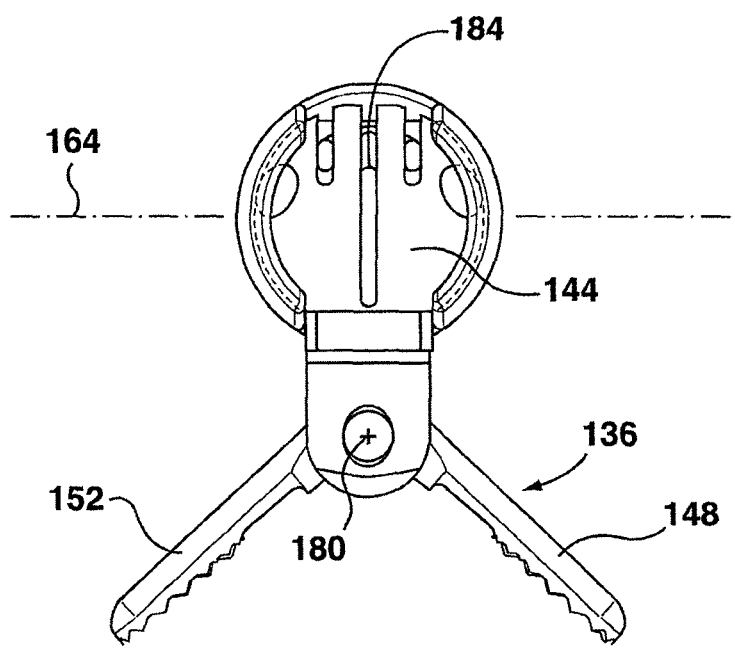
FIG. 3 is another perspective view of the robotic instrument with the working member in an open position in accordance with the embodiment of FIG. 2.
Figure 4:
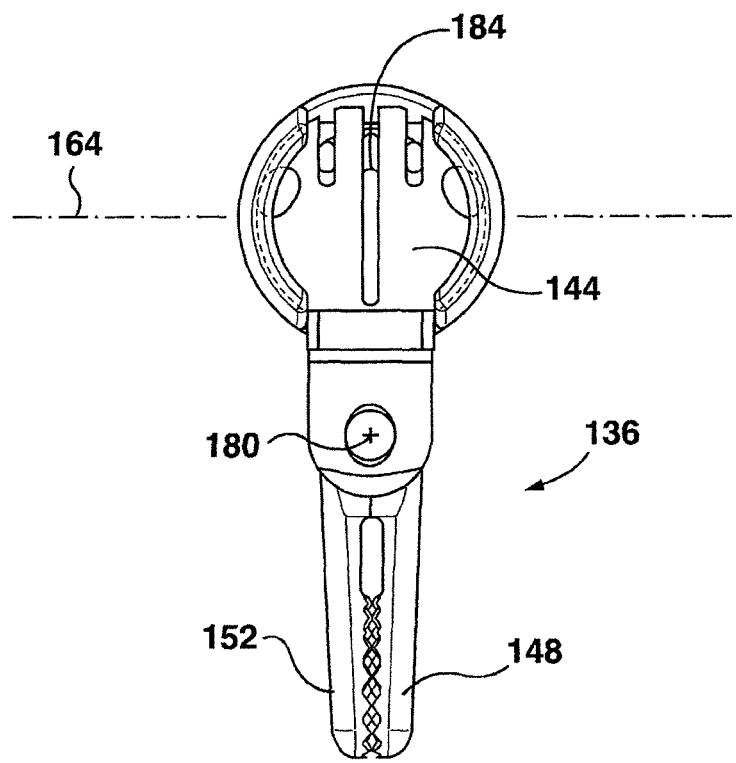
FIG. 4 is another perspective view of the robotic instrument with the working member in a closed position in accordance with the embodiment of FIG. 2.
Figure 5:
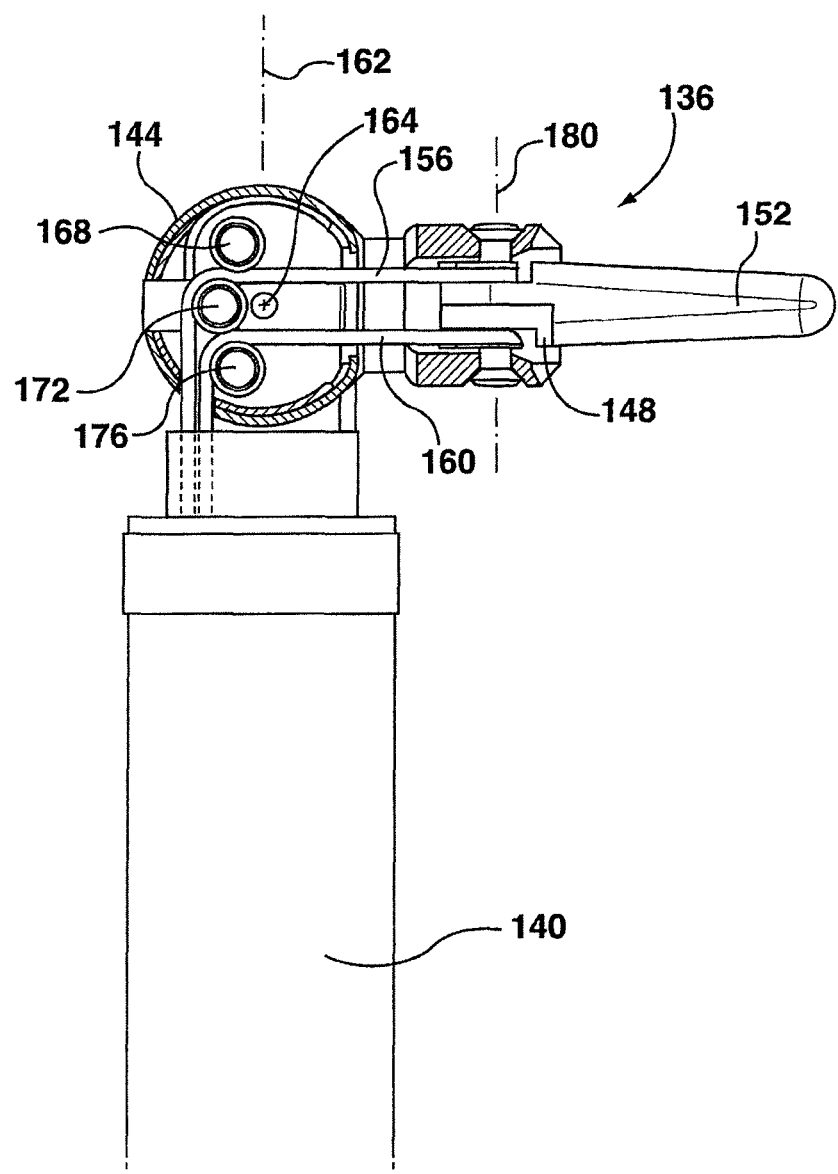
FIG. 5 is a schematic view of the internal parts of the robotic instrument of FIG. 2 in a first position.
Figure 6:
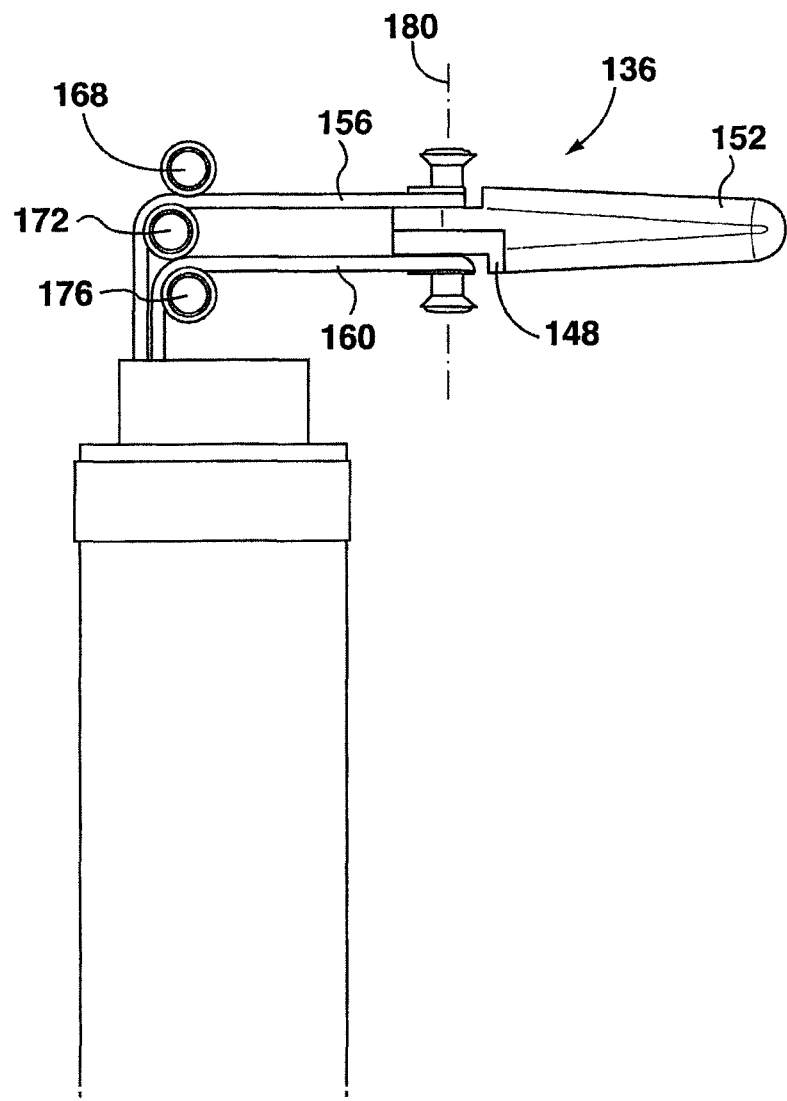
FIG. 6 is another schematic view of the internal parts of the robotic instrument of FIG. 2 in a first position.
Figure 7:
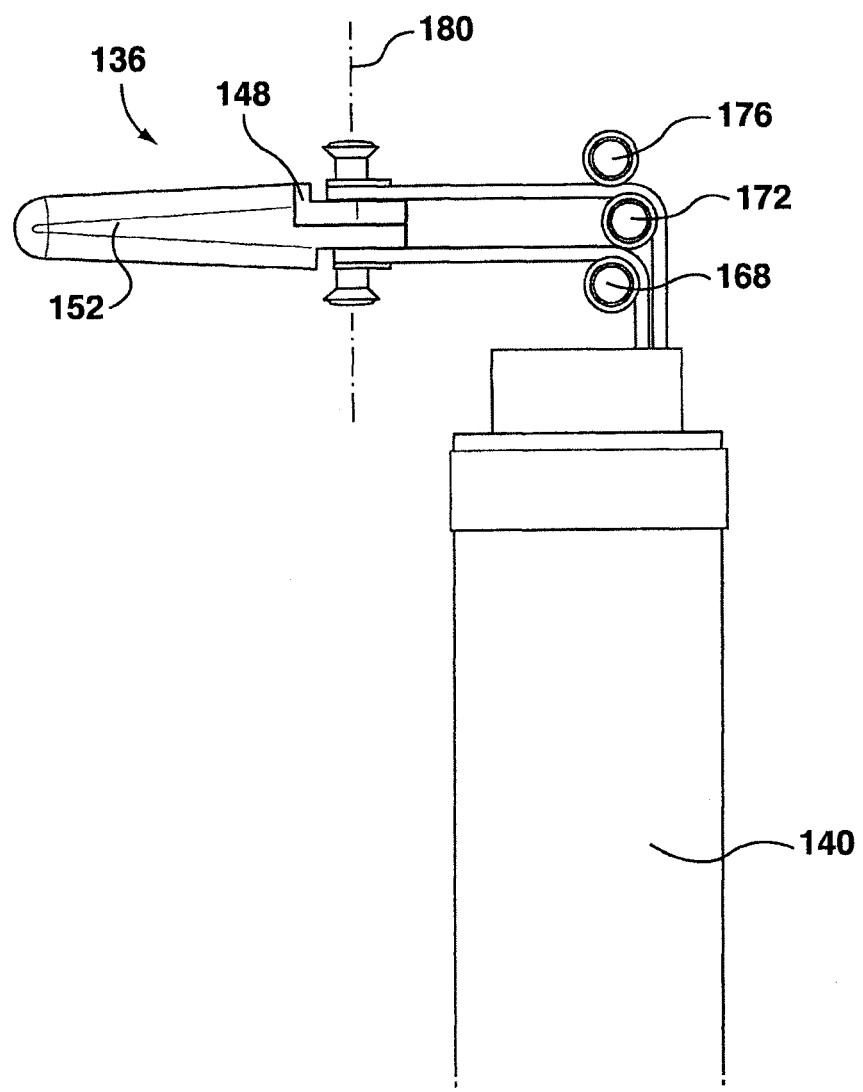
FIG. 7 is a schematic view of the internal parts of the robotic instrument of FIG. 2 in a second position.
Figure 8:
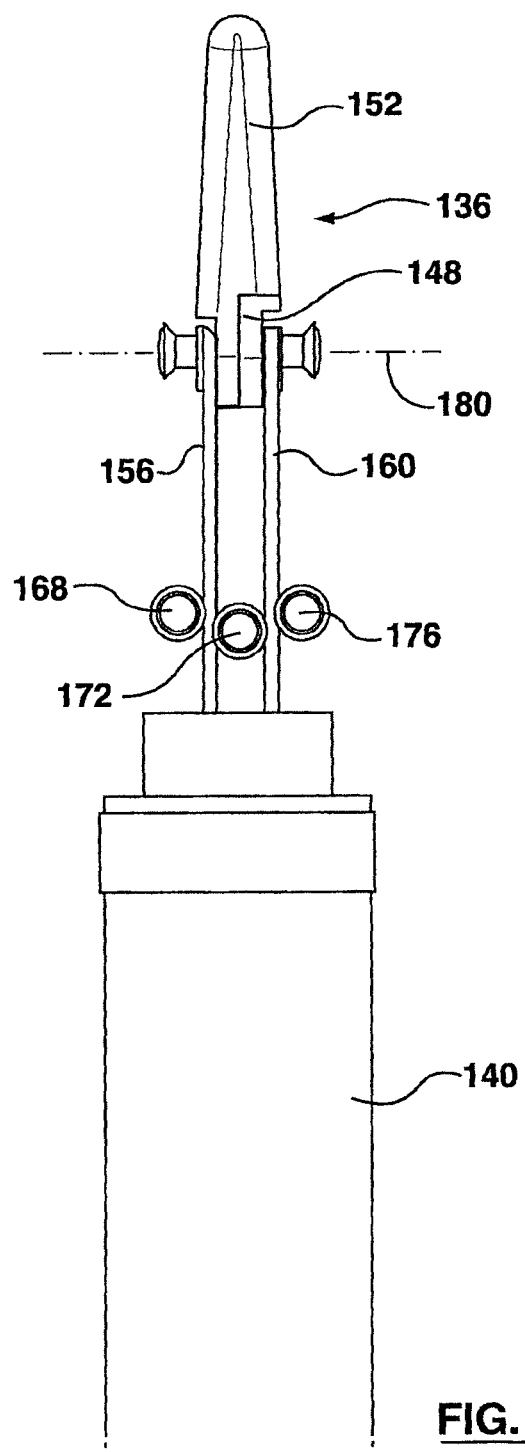
FIG. 8 is a schematic view of the internal parts of the robotic instrument of FIG. 2 in an intermediary position.
Figure 10:
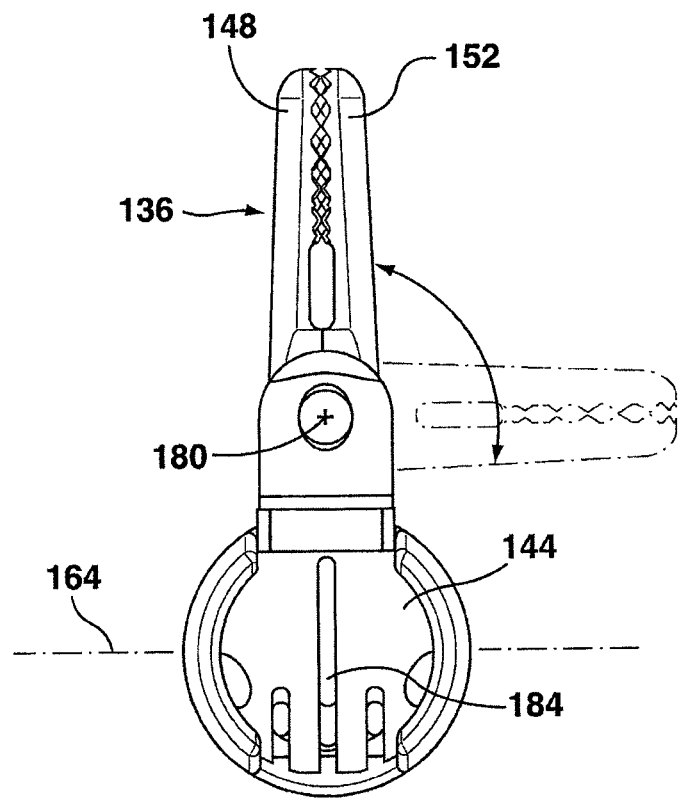
FIG. 10 is a view showing the rotation of the working members of the robotic instrument of FIG. 2.

By controlling the working members 148 and 152, it is to be understood that the working members can be open, as in FIG. 3, or closed, as in FIG. 4. It will now be appreciated by a person skilled in the art with the benefit of this description and the accompanying drawings that, in the present embodiment, the working members 148 and 152 can be pivoted about the second axis 180 as shown in FIG. 10. Furthermore, it will now be appreciated that the ability of the working members 148 and 152 to rotate about the second axis 180 provide a degree of freedom as shown in FIG. 10. Therefore, the independent control of the working members 148 and 152 allows the working members to open and close over a range of angles about the second axis 180.

Figure 11:
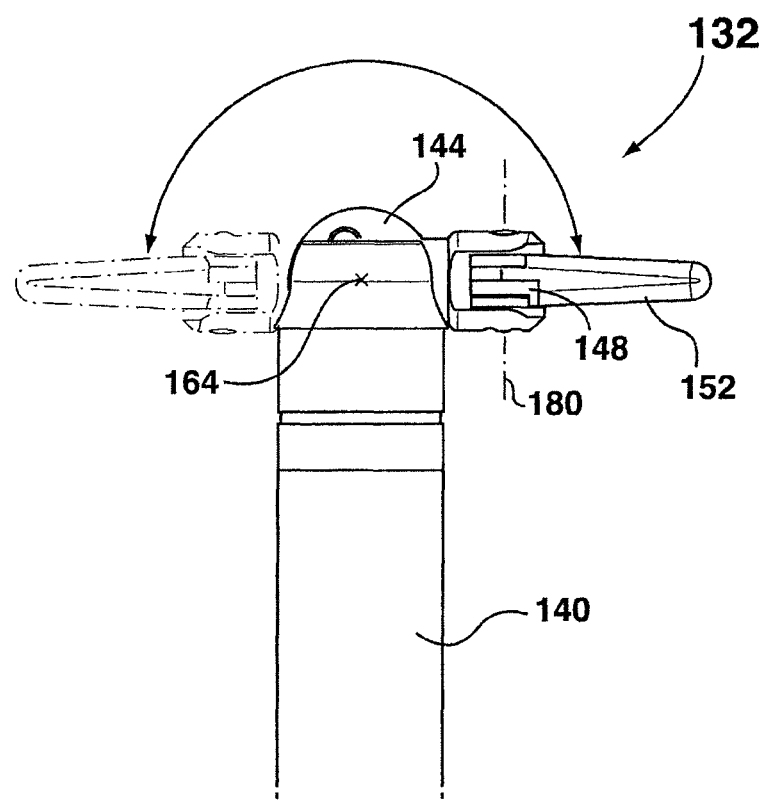
FIG. 11 is a view showing the rotation of the rotatable element of the robotic instrument of FIG. 2.

It will now be appreciated that rotating the rotatable element 144 about the first axis 164, as discussed above, will move the end-effector assembly 136 about the first axis 164 as well. Therefore, the working members 148 and 152 will rotate about the first axis 164 to provide an additional degree of freedom as shown in FIG. 11.

It will now be appreciated that, for uses where a cauterizer is required, the robotic instrument can be used to cauterize tissue. In the present embodiment, the first and second sets of cables 156 and 160 are made of an electrically conductive material. Therefore, the first and second sets of cables 156 and 160 can supply an electrical current to working members 148 and 152 respectively. The electrical current can be used to generate heat at the working members 148 and 152 to cauterize tissue. It will now be appreciated that by using an insulating material for the rotatable element 144, the rotatable element can operate to prevent the first and second set of cables 156 and 160 from short circuiting.

Figure 12:
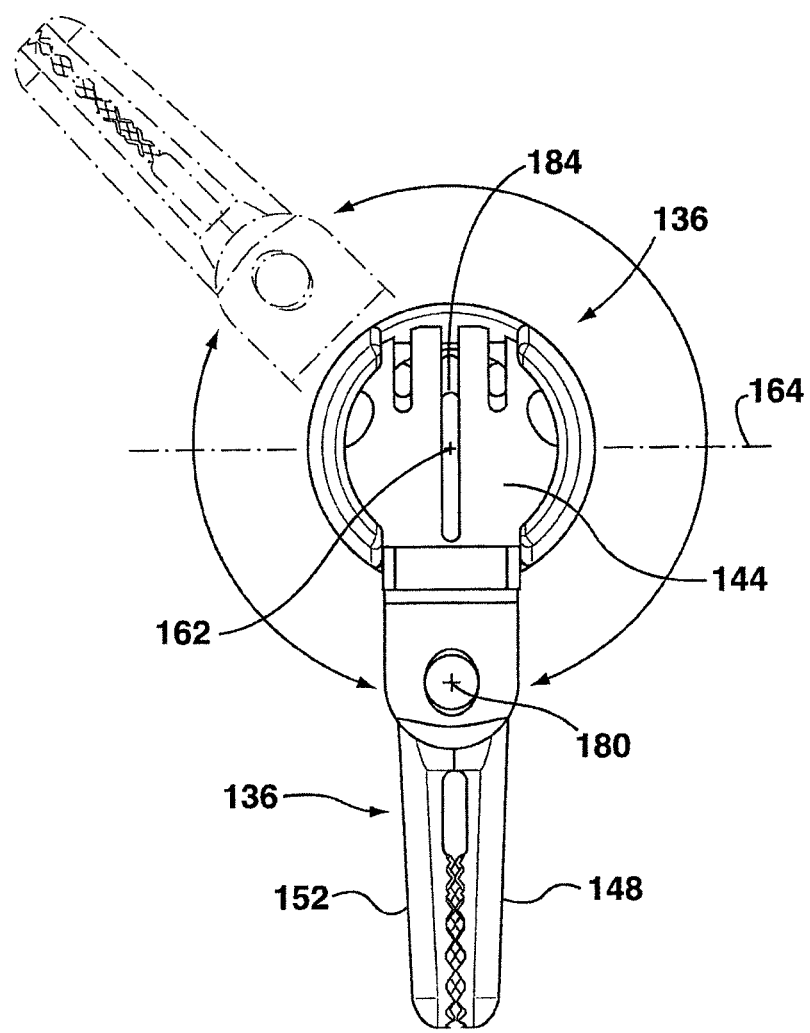
FIG. 12 is a view showing the roll motion of the robotic instrument of FIG. 2.

In addition, it will now be appreciated that the elongated element 140 can be independently rotated to cause the end-effector assembly 136 to rotate about the axis 162. This rotation provides an additional degree of freedom for the robotic instrument 132 which involves rotating the working members 148 and 152 about the axis 162 as shown in FIG. 12. This specific degree of freedom is referred to as a roll motion.

Figure 13:
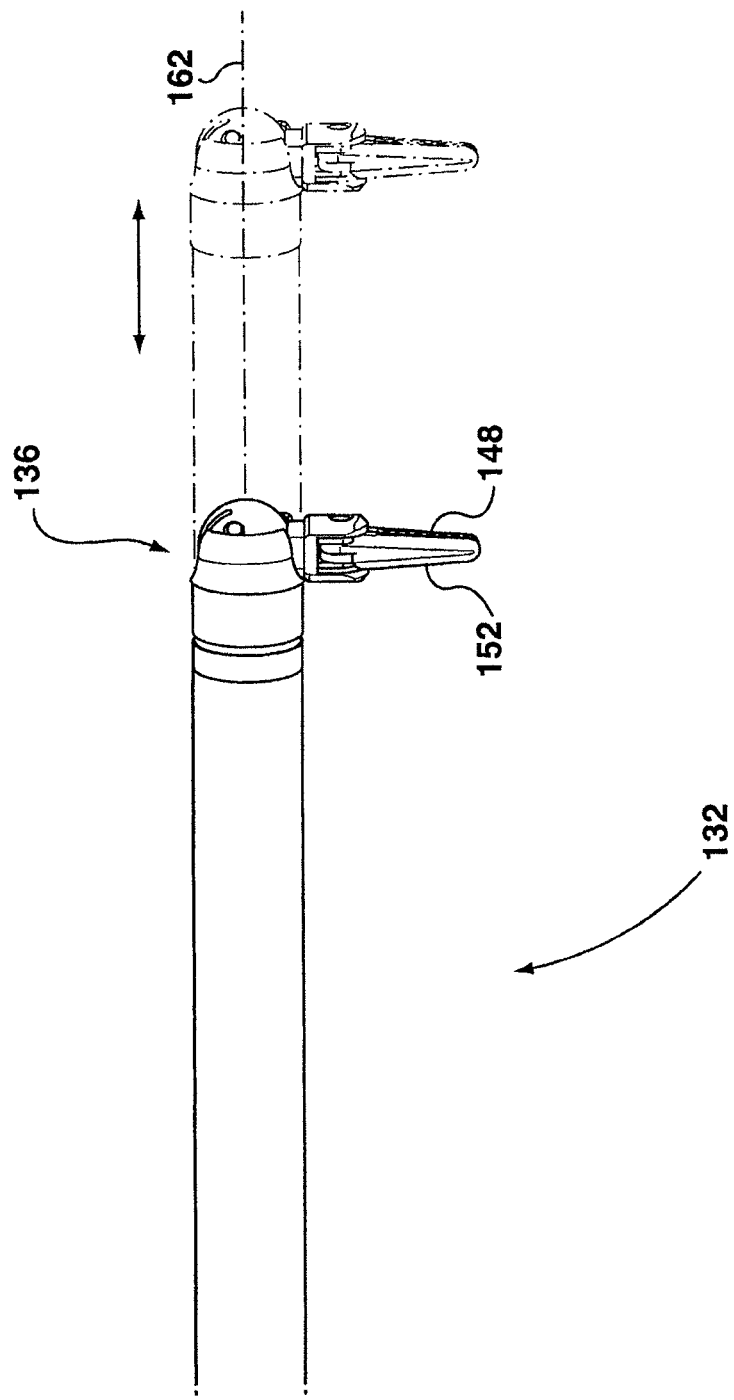
FIG. 13 is a view showing the translational movement of the robotic instrument of FIG. 2.

FIG. 13 shows another degree of freedom involving a longitudinal translation motion allowing the robotic instrument 132 to be translated along the axis 162. For example, this allows the robotic instrument 132 to enter and penetrate deeper into the body of the patient P, or be retracted out of the body. This translational degree of freedom is provided by a system on the robotic arm 128. For example, the robotic arm can include a z-rail system (not shown) for moving the entire robotic instrument 132. However, it is contemplated that the elongated element 140 can be modified to include telescoping functionality.

Figure 14:
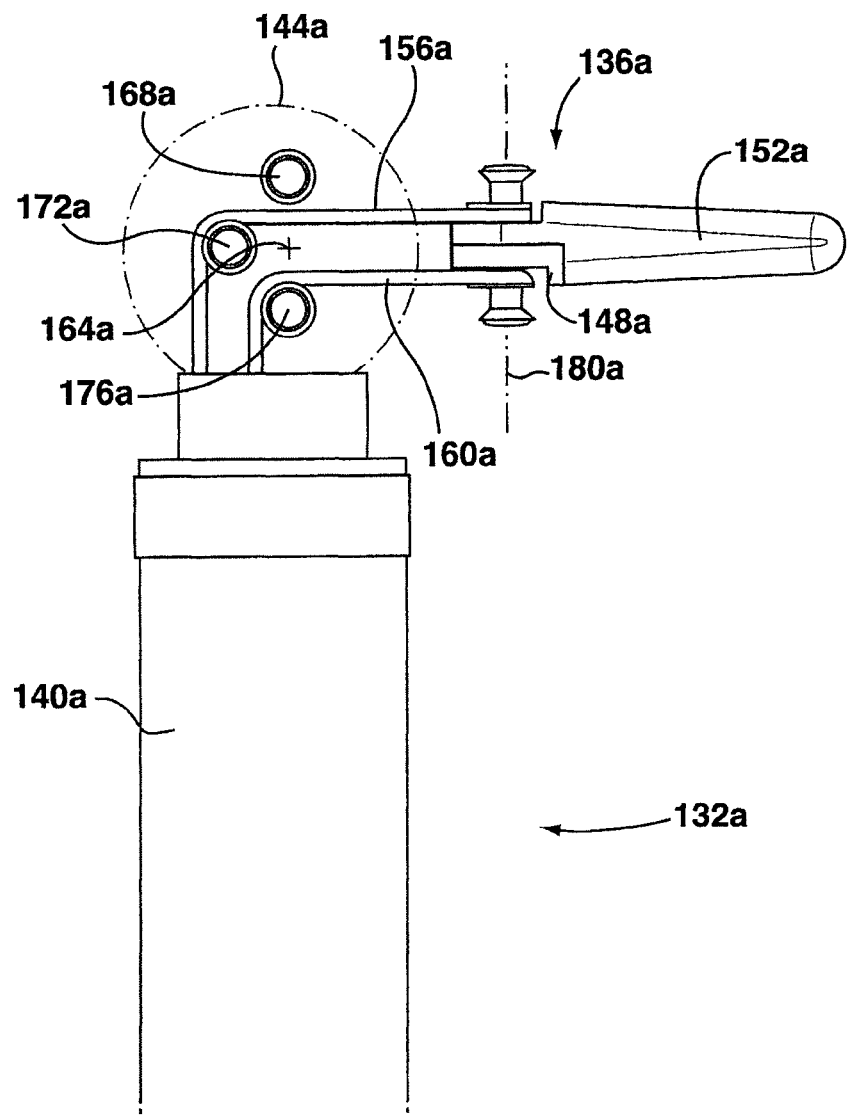
FIG. 14 is a view of the parts of a robotic instrument in accordance with another embodiment in a first position.
Figure 15:
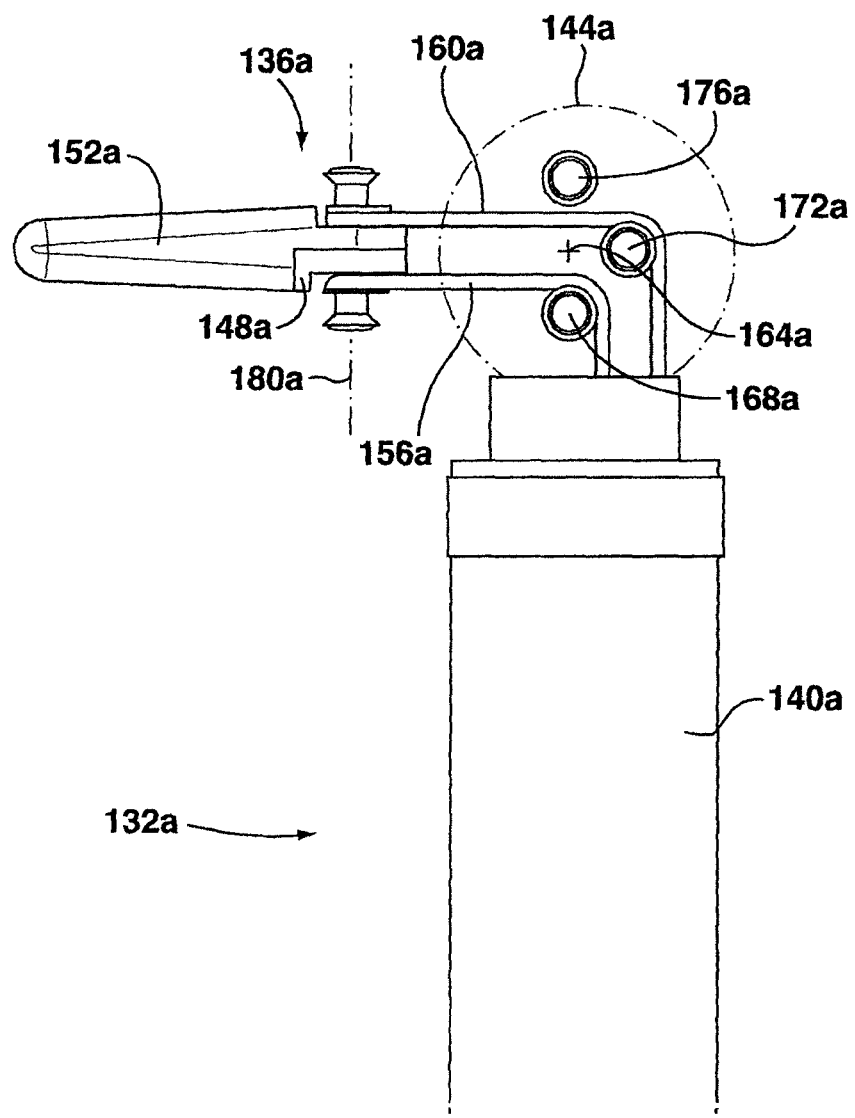
FIG. 15 is a view of the parts of a robotic instrument in accordance with another embodiment in a second position.
Figure 16:
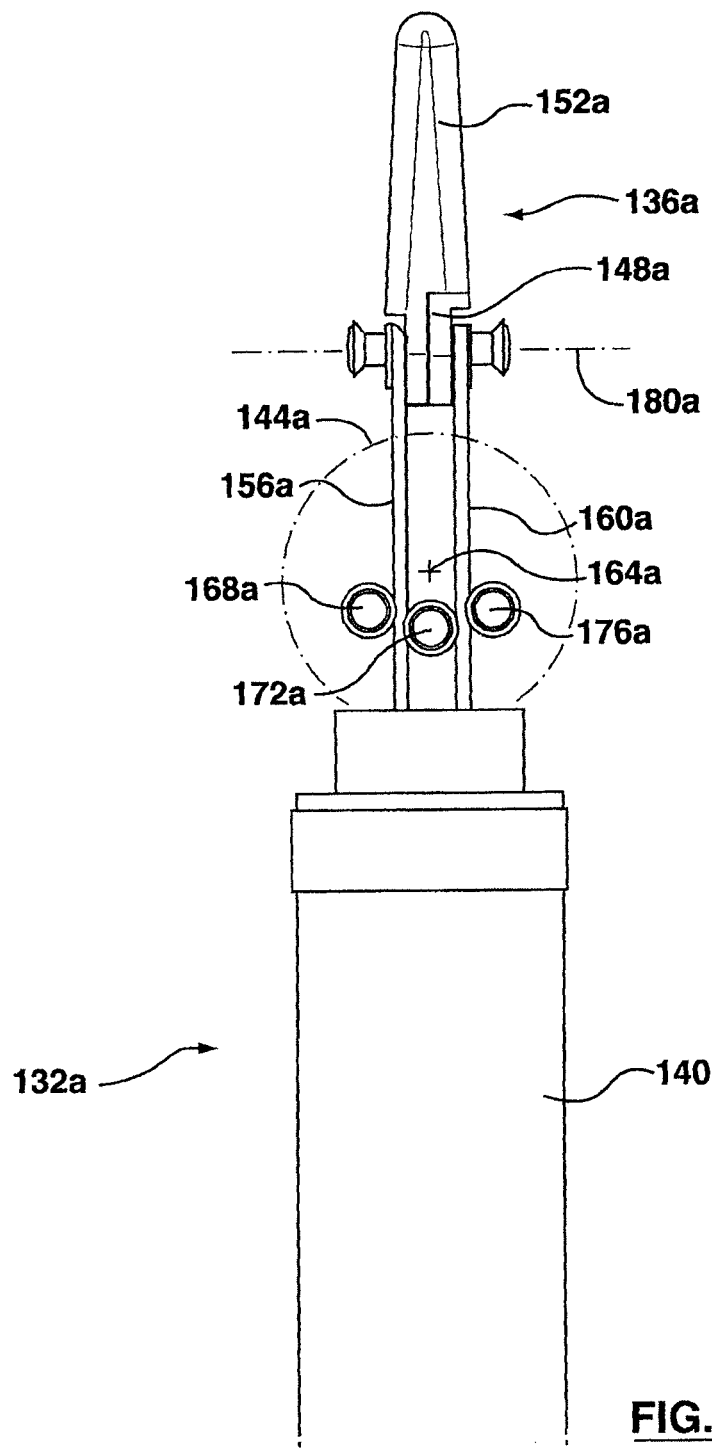
FIG. 16 is a view of the parts of a robotic instrument in accordance with another embodiment in an intermediary position.

Referring to FIGS. 14 to 16, another embodiment of a robotic instrument 132a is schematically shown. Like components of the robotic instrument 132a bear like reference to their counterparts in the robotic instrument 132, except followed by the suffix "a". The robotic instrument 132a includes an end-effector assembly 136a, an elongated element 140a, and a rotatable element 144a.

The end-effector assembly 136a includes two working members 148a and 152a. It is to be understood that the end-effector assembly 136a, including the working members 148a and 152a, is not particularly limited to any material and that several different types of materials are contemplated such as those contemplated for the end-effector assembly 136. The exact configuration of working members 148a and 152a is also not particularly limited. In the present embodiment shown in FIGS. 14 to 16, the working members 148a and 152a are jaws of forceps. In other embodiments, the working members can be imaging equipment, such as a camera or light, or other surgical instruments, such as scissors, blades, needles, catheters, spatulas or cauterizers or combinations thereof.

Referring to FIG. 14, the elongated element 140a extends between the end-effector assembly 136a and the robotic instrument base (not shown). The elongated element 140a is generally configured to support the end-effector assembly 136a and to guide first and second sets of cables 156a and 160a from the robotic instrument base to the end-effector assembly 136a. The first and second set of cables 156a and 160a can comprise a single cable or a plurality of cables. Furthermore, it is to be understood that the elongated element 140a and the first and second set of cables 156a and 160a are not particularly limited to any material and that several different types of surgical-grade materials are contemplated.

The rotatable element 144a of the present embodiment is generally configured to rotate about a first axis 164a and to support first, second and third pulleys 168a, 172a and 176a as well as the working members 148a and 152a of the end-effector assembly 136a. The first, second and third pulleys 168a, 172a and 176a are generally configured to guide the first and second set of cables 156a and 160a such that the cables can move with little friction when the end-effector assembly 136a is in various positions. In the present embodiment, the first, second and third pulleys 168a, 172a and 176a are spaced apart such that the first set of cables 156a will only engage no more than one of the first and second pulleys 168a and 172a for any given position of the end-effector assembly 136a. Furthermore, the second set of cables 160a will only engage no more than one of the second and third pulleys 172a and 176a for any given position of the end-effector assembly 136a. By reducing the number of pulleys the first and second set of cables 156a and 160a can contact, the overall amount of friction is reduced to provide for easier control of the working members 148a and 152a by the first and second set of cables. It is to be understood that the rotatable element 144a is not particularly limited to any material and that several different types of surgical-grade materials are contemplated such as those contemplated for the rotatable element 144.

In operation, the present embodiment of the robotic instrument 132a controls the movement of the working members 148a and 152a of the end-effector assembly 136a in a similar manner as the robotic instrument 132. The first set of cables 156a is generally configured to control motion of the first working member 148a about a second axis 180a. In the present embodiment the first set of cables includes a pair of cables. Each of the pair of cables is connected to the first working member 148a such that the two cables would provide torque in opposite directions when tension is applied to the cable. Therefore, applying tension to one cable will apply a torque to the working member 148a in a first direction about the second axis 180a and applying tension to the other cable will apply a torque to the working member 148a in a second direction about the second axis 180 that is opposite to the first direction. The second set of cables 160a is generally configured to control motion of the second working member 152a about the second axis 180a. It is to be understood that the second set of cables 160a can be controlled independently from the first set of cables 156a.

In addition, the rotatable element 144a can be controlled with a third set of cables (not shown). The third set of cables can rotate the control the rotatable element 144 in substantially the same manner the first and second set of cables 156a and 160a controls the first and second working members 148a and 152a, respectively. Therefore, the rotatable element 144a can be positioned at a variety of angles including a first position (shown in FIG. 14), a second position (shown in FIG. 15), and an intermediate position (shown in FIG. 16). In the present embodiment, the first, second and third pulleys 168a, 172a and 176a are spaced apart such that up to two of first, second and third pulleys 168a, 172a and 176a guide the first and second set of cables 156 and 160 regardless of the position of the rotatable element 144a. For example, when the rotatable element 144a, including the first, second and third pulleys 168a, 172a and 176a, is in the first position, the second pulley 172a guides the first set of cables 156a and the third pulley 176a guides the second set of cables 160a. When the rotatable element 144a, including the first, second and third pulleys 168a, 172a and 176a, is in the second position, the second pulley 172a guides the second set of cables 160a and the first pulley 168a guides the first set of cables 156a. In the intermediate position of the present embodiment shown in FIG. 13, the second pulley 172a guides the first and second set of cables 156a and 160a while the first and second pulleys 168a and 176a are not in contact with either set of cables. It will now be appreciated that in other embodiments the rotatable element 144a can be modified such that the spacing of the first, second and third pulleys 168a, 172a, and 176a allows the first and second set of cables 156a and 160a to not contact any pulley while in the intermediate position. Alternative, it is also to be understood that the rotatable element 144a can be modified such that the spacing of the first, second and third pulleys 168a, 172a, and 176a causes the first and second set of cables 156a and 160a to contact the first and third pulleys 168a and 172a, respectively while in the intermediate position.

Figure 17:
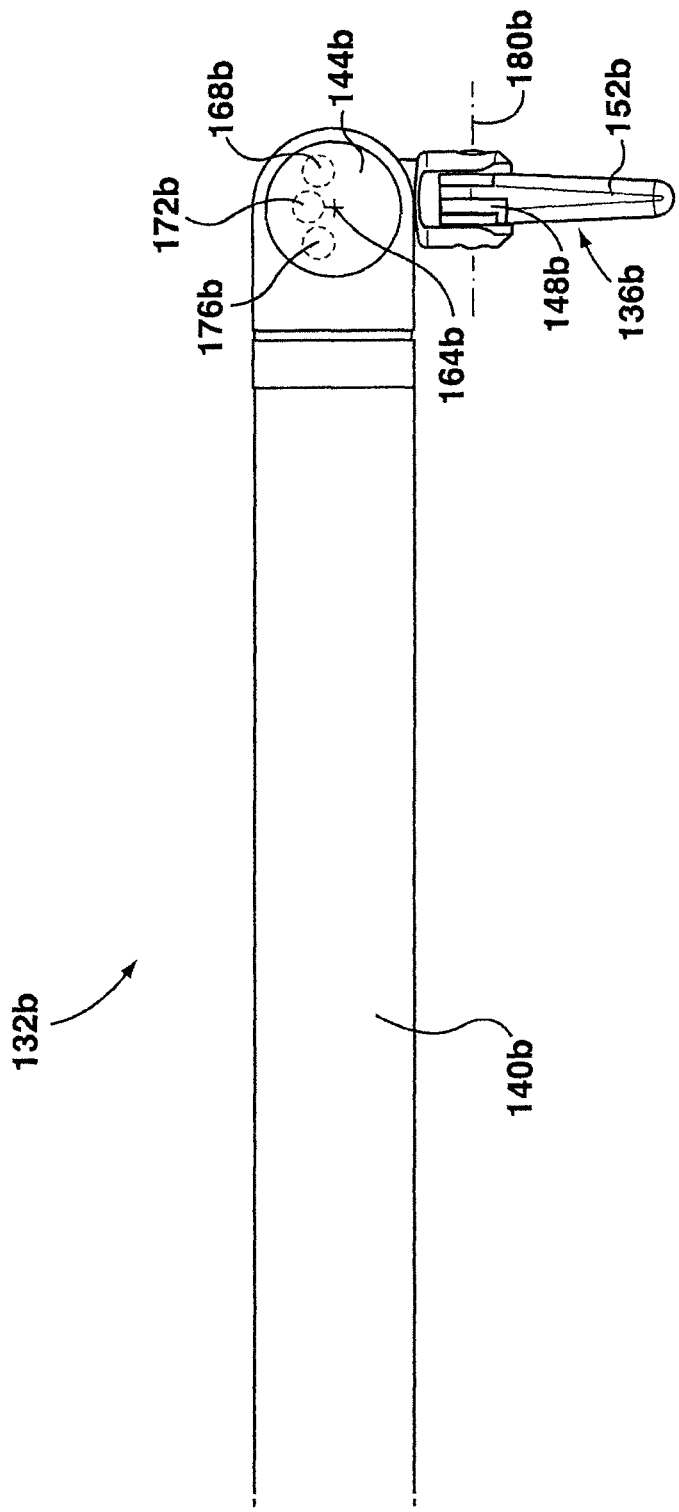
FIG. 17 is a perspective view of a robotic instrument in accordance with another embodiment.
Figure 18:
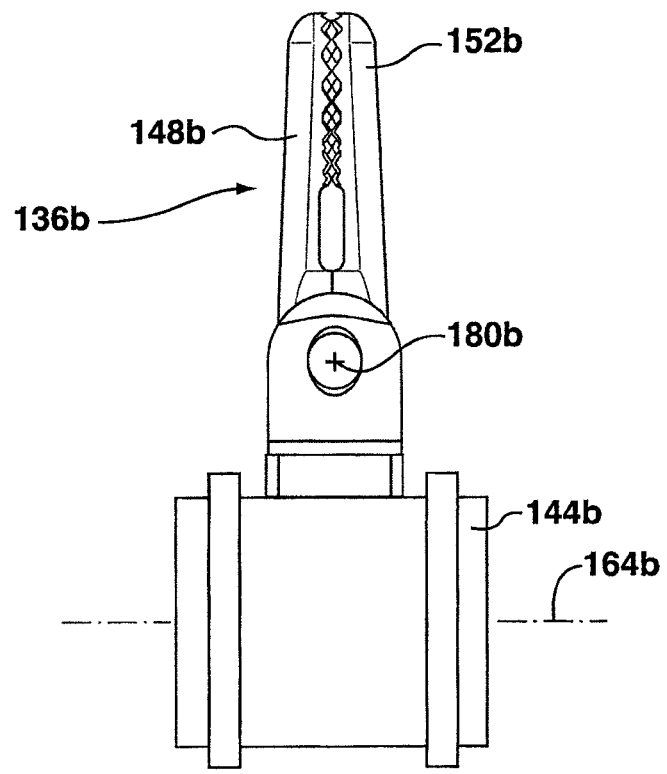
FIG. 18 is another perspective view of the robotic instrument in accordance with the embodiment of FIG. 17.

Referring to FIGS. 17 to 18, another embodiment of a robotic instrument 132b is schematically shown. Like components of the robotic instrument 132b bear like reference to their counterparts in the robotic instruments 132 and 132a, except followed by the suffix "b". The robotic instrument 132b includes an end-effector assembly 136b, an elongated element 140b, and a rotatable element 144b.

The end-effector assembly 136b includes two working members 148b and 152b. It is to be understood that the end-effector assembly 136b, including the working members 148b and 152b, is not particularly limited to any material and that several different types of materials are contemplated such as those contemplated for the end-effector assembly 136 and 136b. The exact configuration of working members 148b and 152b is also not particularly limited. In the present embodiment shown in FIGS. 17 to 18, the working members 148b and 152b are jaws of forceps. In other embodiments, the working members can be imaging equipment, such as a camera or light, or other surgical instruments, such as scissors, blades, needles, catheters, spatulas or cauterizers or combinations thereof.

Referring to FIG. 17, the elongated element 140b extends between the end-effector assembly 136b and the robotic instrument base (not shown). The elongated element 140b is generally configured to support the end-effector assembly 136b and to guide first and second sets of cables 156b and 160b from the robotic instrument base to the end-effector assembly 136b. The first and second set of cables 156b and 160b can comprise a single cable or a plurality of cables. Furthermore, it is to be understood that the elongated element 140b and the first and second set of cables 156b and 160b are not particularly limited to any material and that several different types of surgical-grade materials are contemplated.

The rotatable element 144b of the present embodiment is generally cylindrical such that the axis of the cylindrical portion coincides with a first axis 164b. The rotatable element 144b is configured to rotate about a first axis 164b and to support first, second and third pulleys 168b, 172b and 176b as well as the working members 148b and 152b of the end-effector assembly 136b. The first, second and third pulleys 168b, 172b and 176b are generally configured to guide the first and second set of cables 156a and 160a such that the cables can move with little friction when the end-effector assembly 136a is in various positions.

In operation, the present embodiment of the robotic instrument 132b controls the movement of the working members 148b and 152b of the end-effector assembly 136b in a similar manner as the robotic instruments 132 and 132a. The first set of cables 156b is generally configured to control motion of the first working member 148b about a second axis 180b. The second set of cables 160b is generally configured to control motion of the second working member 152b about the second axis 180b. It is to be understood that the second set of cables 160b can be controlled independently from the first set of cables 156b.

Figure 19:
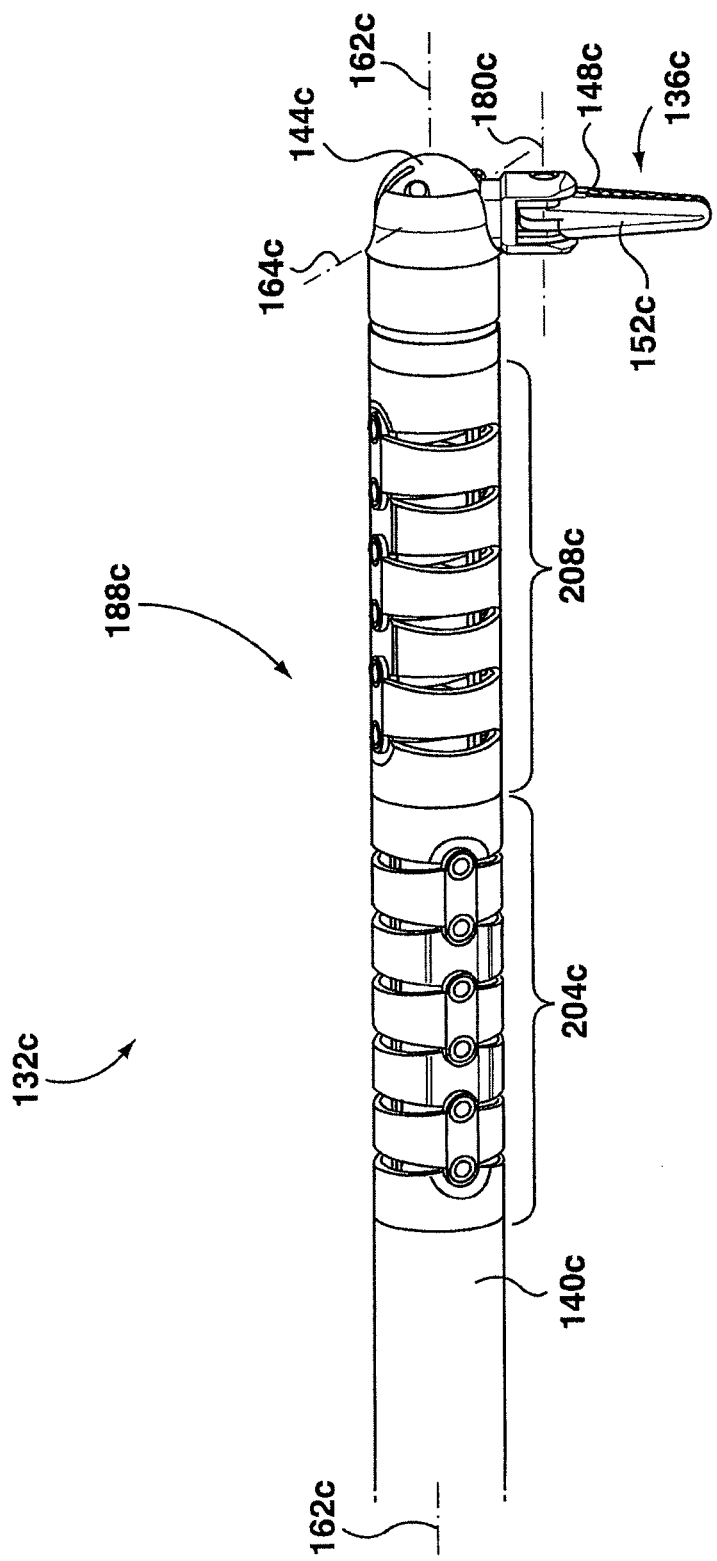
FIG. 19 is a perspective view of a robotic instrument in accordance with another embodiment.

Referring to FIG. 19, another embodiment of a robotic instrument 132c is shown. Like components of the robotic arm 132c bear like reference to their counterparts, except followed by the suffix "c". The robotic instrument 132c includes an end-effector assembly 136c, an elongated element 140c, and a rotatable element 144c. In this particular embodiment, the robotic instrument 132c includes a flexible portion 188c configured to provide coarse motion proximate to the end-effector assembly 136c. The flexible portion 188c is located between the elongated element 140c and the end-effector assembly 136c.

The flexible portion 188c includes first and second subsections 204c and 208c. Each of the first and second subsections 204c and 208c is generally configured to bend within first and second coarse motion planes, respectively. In some embodiments, the flexible portion 188c may also have a second elongated element (not shown) extending to the end effector assembly 136c to provide further support. The second elongated element includes a flexible portion which can be provided by using laser cutting techniques. Laser cut elongated elements may be obtained from Pulse Systems (Concord, Ontario, Canada) using uncut stainless steel tubes from VitaNeedle (Needham, Mass., U.S.A.). Alternatively, the second elongated element can include a flexible coiled portion. Furthermore, the motion of the first subsection 204c and the second subsection 208c are independent such that one or both of the first and second subsections may be bent independently. Therefore, it is to be understood that the coarse motion of the robotic instrument 132c can be controlled using a set of at least one course motion adjustment cable (not shown) for each of subsection 204c and 208c by independently adjusting the tension of each set of at least one course motion adjustment cable.

Referring again to FIG. 19, in the present embodiment, the first and second coarse motion planes are substantially perpendicular to each other. However, it is to be appreciated that the first and second coarse motion planes do not need to be perpendicular to each other and may be at any angle in some embodiments. Furthermore, the exact configuration of first and second subsections 204c and 208c is not particularly limited. In the present embodiment, there are two subsections 204c and 208c. In other embodiments, it is to be understood that the flexible portion 188c can be modified to include more subsections to provide more coarse motion planes within which subsections of the flexible portion 188c can bend. Alternatively, it is also to be understood that the flexible portion 188c can be modified to include only one subsection to provide a single coarse motion plane.

It will now be appreciated that each subsection will provide an additional degree of freedom. Referring back to FIG. 19, it will now be apparent that the first and second subsections 204c and 208c add two more degrees of freedom to the robotic instrument 132c. Therefore, the robotic instrument 132c includes six degrees of freedom. The six degrees of freedom include the roll about the axis 162c, rotation of the end-effector assembly 136c about a first axis 164c, rotation of a first working member 148c about a second axis 180c, rotation of a first working member 152c about the second axis 180c, the bending of the first subsection 204c and the bending of the second subsection 208c. In addition, the entire robotic instrument may be moved on a rail system (not shown) to provide a seventh degree of freedom.

It is to be understood that combinations, variations and subsets of the embodiments and teachings herein are contemplated. As a non-limiting example, robotic instrument 132b can be combined with the variation described in relation to the robotic instrument 132c to provide coarse motion to the robotic instrument 132b.

While specific embodiments have been described and illustrated, such embodiments should be considered illustrative only and should not serve to limit the accompanying claims.

What is claimed is:

1. An apparatus for controlling an end-effector assembly having a first working member and a second working member, the apparatus comprising:
   a first set of at least one cable, the first set of at least one cable configured to control the first working member;
   a second set of at least one cable, the second set of at least one cable configured to control the second working member;
   a first pulley configured to guide the first set of at least one cable;
   a second pulley having a pulley groove configured to guide the first set of at least one cable within the pulley groove when the second pulley is in a first position, and the second pulley configured to guide the second set of at least one cable within the pulley groove when the second pulley is in a second position;
   a third pulley configured to guide the second set of at least one cable; and
   a rotatable element rotatable about a first axis, the rotatable element supporting the first pulley, the second pulley, the third pulley, and the first and second working members, and the rotatable element configured to move the second pulley between the first position and the second position.

2. The apparatus of claim 1, wherein the first pulley, the second pulley, and the third pulley are configured to rotate in a first pulley plane.

3. The apparatus of claim 1, further comprising a third set of at least one cable, the third set of at least one cable configured to rotate the rotatable element about the first axis to adjust a rotation about the first axis.

4. The apparatus of claim 1, wherein the rotatable element comprises a ball portion, the ball portion configured to rotate in a socket.

5. The apparatus of claim 1, wherein the rotatable element comprises an insulating material.

6. The apparatus of claim 1, further comprising a first pair of pulleys, the first pair of pulleys comprising the first pulley and a fourth pulley.

7. The apparatus of claim 1, further comprising a second pair of pulleys, the second pair of pulleys comprising the second pulley and a fifth pulley.

8. The apparatus of claim 1, wherein the rotatable element comprises a cylindrical portion, wherein an axis of the cylindrical portion coincides with the first axis.

9. The apparatus of claim 8, further comprising a second pair of pulleys, the second pair of pulleys comprising the second pulley and a fifth pulley.

10. The apparatus of claim 1, wherein at least one set of at least one cable is electrically conductive, the at least one set of at least one cable configured to deliver an electrical current to at least one working member.

11. The apparatus of claim 10, further comprising a second pair of pulleys, the second pair of pulleys comprising the second pulley and a fifth pulley.

12. The apparatus of claim 1, further comprising a third pair of pulleys, the third pair of pulleys comprising the third pulley and a sixth pulley.

13. The apparatus of claim 12, wherein the sixth pulley is configured to rotate in a second pulley plane that is perpendicular to the first axis.

14. The apparatus of claim 1, wherein the first pulley is configured to rotate about a first pulley axis, the second pulley is configured to rotate about a second pulley axis, and the third pulley is configured to rotate about a third pulley axis.

15. The apparatus of claim 14, wherein the first pulley axis, the second pulley axis, and the third pulley axis are spaced apart.

16. The apparatus of claim 14, wherein the first pulley axis, the second pulley axis, and the third pulley axis are rotatable about the first axis.

17. The apparatus of claim 14, wherein the rotatable element comprises an insulating material.

18. The apparatus of claim 14, wherein the third pulley and a sixth pulley are configured to rotate about the third pulley axis.

19. The apparatus of claim 14, wherein the first pulley axis, the second pulley axis, and the third pulley axis are equidistant from the first axis.

20. The apparatus of claim 19, wherein the first pulley plane is perpendicular the first axis.

21. The apparatus of claim 14, further comprising a first pair of pulleys, the first pair of pulleys comprising the first pulley and a fourth pulley.

22. The apparatus of claim 21, wherein the first pulley and the fourth pulley are configured to rotate about the first pulley axis.

23. The apparatus of claim 14, further comprising a second pair of pulleys, the second pair of pulleys comprising the second pulley and a fifth pulley.

24. The apparatus of claim 23, wherein the second pulley and the fifth pulley are configured to rotate about the first pulley axis.

* * * * *